US011185216B2

(12) United States Patent
Heni et al.

(10) Patent No.: US 11,185,216 B2
(45) Date of Patent: Nov. 30, 2021

(54) VIDEO ENDOSCOPE AND HANDLE FOR A VIDEO ENDOSCOPE INCLUDING ROTATIONAL SUPPORT MEANS

(71) Applicant: KARL STORZ SE & Co KG, Tuttlingen (DE)

(72) Inventors: Pascal Heni, Tuttlingen (DE); Markus Kupferschmid, Tuttlingen (DE); Andreas Heni, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 0 days.

(21) Appl. No.: 16/906,947

(22) Filed: Jun. 19, 2020

(65) Prior Publication Data

US 2020/0397228 A1    Dec. 24, 2020

(30) Foreign Application Priority Data

Jun. 22, 2019  (DE) .......................... 102019004433.9

(51) Int. Cl.
*A61B 1/00*  (2006.01)
*A61B 90/00*  (2016.01)
(Continued)

(52) U.S. Cl.
CPC ...... *A61B 1/00124* (2013.01); *A61B 1/00009* (2013.01); *A61B 1/00018* (2013.01);
(Continued)

(58) Field of Classification Search
CPC ............ A61B 1/00124; A61B 1/00009; A61B 1/00018; A61B 1/00027; A61B 1/00066;
(Continued)

(56) References Cited

U.S. PATENT DOCUMENTS 6,030,339 A    2/2000  Tatsuno et al.
6,095,970 A    8/2000  Hidaka et al.
(Continued)

FOREIGN PATENT DOCUMENTS

DE           19925323 A1    12/2000
DE       102012206412 A1    10/2013
(Continued)

OTHER PUBLICATIONS

Neumeyr, T., European Search Report, Ap. EP 20181308, dated Nov. 9, 2020, pp. 1-7, Munich.

*Primary Examiner* — Allen C Wong
(74) *Attorney, Agent, or Firm* — Michael J Loi; David Noel Villalpando

(57) ABSTRACT

The invention concerns a handle for a video endoscope for medical or industrial applications, comprising a housing and an interface portion, where the interface portion includes a first connector element at its distal end connected to an electric transmission element that is connectable to a connector element of an associated elongate shaft to form a detachable electrical and/or mechanical connection between the handle and the associated shaft. The includes an electrical connection assembly arranged at an exterior of the interface portion forming an electrical connection between the electric transmission element and a stationary electric and/or electronic component of the handle. The handle also includes at least a first bearing for rotatably supporting the interface portion in and/or at the housing, such that when the shaft and handle are connected the shaft is rotatable via the rotatably supported interface portion relative to the housing of the handle.

20 Claims, 3 Drawing Sheets

(51) Int. Cl.
  *A61B 1/05* (2006.01)
  *A61B 1/06* (2006.01)
  *G02B 23/24* (2006.01)
  *H01R 39/64* (2006.01)
  *H04N 5/225* (2006.01)

(52) U.S. Cl.
  CPC ...... *A61B 1/00027* (2013.01); *A61B 1/00066* (2013.01); *A61B 1/05* (2013.01); *A61B 1/053* (2013.01); *A61B 1/0661* (2013.01); *A61B 1/0669* (2013.01); *A61B 1/0684* (2013.01); *A61B 90/03* (2016.02); *G02B 23/2484* (2013.01); *H01R 39/643* (2013.01); *H04N 5/2253* (2013.01); *A61B 2090/035* (2016.02); *H01R 2201/12* (2013.01); *H04N 2005/2255* (2013.01)

(58) Field of Classification Search
  CPC ......... A61B 1/05; A61B 1/053; A61B 1/0661; A61B 1/0669; A61B 1/0684; A61B 90/03; A61B 2090/035; G02B 23/2484; H01R 39/643; H01R 2201/12; H04N 5/2253; H04N 2005/2255
  USPC .......................................................... 348/75
  See application file for complete search history.

(56) References Cited

U.S. PATENT DOCUMENTS

| | | | |
|---|---|---|---|
| 7,212,737 | B2 | 5/2007 | Dehmel et al. |
| 7,241,263 | B2 | 7/2007 | Boulais |
| 7,828,720 | B2 | 11/2010 | Miller et al. |
| 8,187,171 | B2 | 5/2012 | Irion et al. |
| 8,197,400 | B2 | 6/2012 | Boutillette et al. |
| 8,992,424 | B2 | 3/2015 | Orbay et al. |
| 9,107,573 | B2 | 8/2015 | Bimkrant |
| 9,907,457 | B2 | 3/2018 | Grant et al. |
| 10,365,470 | B2 | 7/2019 | Wieters et al. |
| 2006/0058581 | A1 | 3/2006 | Hanke |
| 2008/0300456 | A1 | 12/2008 | Irion et al. |
| 2010/0125166 | A1 | 5/2010 | Henzler |
| 2011/0193948 | A1 | 8/2011 | Amling et al. |
| 2011/0306834 | A1 | 12/2011 | Schrader et al. |
| 2014/0221749 | A1 | 8/2014 | Grant et al. |
| 2014/0357952 | A1 | 12/2014 | Krohn et al. |
| 2015/0085093 | A1 | 3/2015 | Heni et al. |
| 2015/0105620 | A1 | 4/2015 | Orginski et al. |
| 2017/0055992 | A1* | 3/2017 | Widenhouse ...... A61B 17/1219 |
| 2017/0209024 | A1 | 7/2017 | Weitzner et al. |
| 2019/0374095 | A1* | 12/2019 | Lord .................. A61B 1/00066 |
| 2021/0137355 | A1* | 5/2021 | Lund ..................... A61B 1/012 |

FOREIGN PATENT DOCUMENTS

| | | |
|---|---|---|
| DE | 102017119691 A1 | 2/2019 |
| WO | 00/57770 A2 | 10/2000 |
| WO | 2011143269 A1 | 11/2011 |

\* cited by examiner

VIDEO ENDOSCOPE AND HANDLE FOR A VIDEO ENDOSCOPE INCLUDING ROTATIONAL SUPPORT MEANS

CROSS REFERENCE TO RELATED APPLICATIONS

This application claims priority to German Patent Application No. 102019004433.9, filed Jun. 22, 2019, and entitled, "Video endoscope and handle for a video endoscope," and is incorporated herein by reference.

FIELD OF THE INVENTION

The invention concerns a handle for a video endoscope, in particular for a medical or industrial video endoscope, comprising a housing and an interface portion, wherein the interface portion comprises a first connector element at its distal end, the first connector element is connected to an electric transmission element of the interface portion and is connectable to a second connector element of an associated elongate shaft of the video endoscope to form a detachable electrical and/or mechanical connection between the handle and the associated shaft, and wherein the handle comprises an electrical connection assembly arranged at an exterior of the interface portion forming an electrical connection between the electric transmission element and a stationary electric and/or electronic component of the handle. Furthermore, the invention concerns a video endoscope.

BACKGROUND OF THE INVENTION

For medical or non-medical applications, endoscopes comprise an elongate shaft configured for being introduced into an internal cavity of a human or animal body or another object for examination. For generating an image of an object field in the cavity of the body or object, an imaging optic is located in a distal (meaning distant from a user) end section of the shaft. On the opposite, proximal (meaning close to the user) end section of the shaft, a handle is attached for operating the endoscope by the user. In case of video endoscopes, which are also known as electronic endoscopes, the generated endoscopic image is picked up by an electronic image sensor, whereby, in a wide-spread design, the electronic image sensor together with the imaging optics are contained in an optic shaft arranged inside the shaft of the video endoscope. Consequently, the image signal generated by the image sensor is transmitted electronically through the shaft and the handle towards the proximal end of the video endoscope and outwards for displaying the endoscopic image on a monitor.

Common video endoscopes are complete systems, wherein the shaft and the handle are permanently fixed to each other. As a complete system, the whole video endoscope must be cleaned and sterilized (generally in an autoclave) after each use. Furthermore, during an endoscopic procedure, user is frequently required to change a rotational orientation of the endoscope in order to vary the view of the object field, and in with the limitations of conventional video endoscopes, the complete video endoscope must be rotated during examination. As such, the operator controls, buttons or touch keys, which are usually arranged at the top side of the handle in its upright position, are arranged in an unfavorable position for the user during rotation. This design is especially disadvantageous, because normally the handle is held by the same hand of the user that likewise operates the operator buttons or touch keys.

As, in a video endoscope, the electronic image sensor is stationary and generally mounted in the shaft, most commonly at the distal end of the shaft, the image sensor will always rotate together with the rotation of the shaft, while, from a user point of view and for ergonomic reasons, it would be preferable to keep an orientation of the handle unchanged during the rotation of the shaft, as is generally the case with proximal detection endoscopic systems, where the image light is transmitted through the shaft, and detected by a sensor contained within the handle or camera head element. While in certain systems, problems associated with the rotation of an image displayed to the user as a result of the rotating sensor can be solved, as is known in the art, by an image processing unit configured for erecting the image displayed on the viewing monitor, in contrast the rotation of the handle itself remains disadvantageous.

US 2017/0209024 A1 discloses an endoscopic device which comprises a shaft including a controllable bend, a lumen and a controllable channel moveably set in the lumen as well as a handle including a controller selectively engageable with the controllable bend and the controllable channel. Inside the shaft, actuators are housed including each an opposing pair of motorized rollers mounted in the lumen for translational movement of the control channel in the proximal or distal direction as well as for rotational movement. Therefore, US 2017/0209024 A1 only concerns the movement and rotation of a control channel relative to a lumen by respectively arranged rollers.

In U.S. Pat. No. 10,365,470 B2, an endoscope is described with an endoscope shaft which comprises an outer tube and an inner tube rotate relative to each other, whereby an axial bearing is arranged between the outer tube and the inner tube in a proximal region of the endoscope shaft, and a radial bearing is arranged between the inner tube and the outer tube in the distal region of the endo scope shaft, wherein the axial bearing is fixed by a fixing device including an elastomer body. Therewith, U.S. Pat. No. 10,365,470 B2 likewise only concerns a rotation within the shaft.

BRIEF DESCRIPTION OF THE INVENTION

The problem is solved by a handle for a video endoscope, in particular for a medical or industrial video endoscope, comprising a housing and an interface portion, wherein the interface portion comprises a first connector element at its distal end, the first connector element is connected to an electric transmission element of the interface portion and is connectable to a second connector element of an associated elongate shaft of the video endoscope to form a detachable electrical and/or mechanical connection between the handle and the associated shaft, and wherein the handle comprises an electrical connection assembly arranged at an exterior of the interface portion forming an electrical connection between the electric transmission element and a stationary electric and/or electronic component of the handle, wherein the handle comprises at least a first bearing for rotatably supporting the interface portion in and/or at the housing so that, in case of a connection between the associated shaft and the handle, the associated shaft is rotatable via the rotatably supported interface portion relatively to the housing of the handle. Therefore, a handle for a video endoscope is provided which permits improved handling and orientation of the video endoscope for a user, especially such that the user can operate the handle of the video endoscope in a manner to which the user has been accustomed. It is particularly beneficial that the orientation of the handle stays essentially constant and, therefore, the operator controls and the handle and its housing are not required to rotate with the rotation of the connected shaft. Therefore, the use of the video endoscope and the navigation by the user inside a body cavity is improved by the inventive handle. Consequently, an endoscopic procedure can be prolonged, and the risk involved in a medical endoscopic intervention is reduced.

As the shaft is connectable via its second connector element to the first connector element of the interface portion of the handle, whereby the interface portion is rotatably supported inside the housing of the handle, the shaft is rotatable together with the interface portion independently and relative to the housing of the handle and therewith independently of the static orientation of the handle. Thus, an efficient and user-friendly handle for a video endoscope is provided, such that a distal tip sensor video endoscope may be handled in a manner similar to traditional endoscopes with a proximal sensor located in an attached camera head.

In addition to allowing the rotation of the video endo scope shaft relative to the instrument handle, the rotatable coupling point comprising the second connector element of the shaft and the first connector element of the interface portion of the handle, also enables a modular video endoscope to be free from the necessity of a permanent, fixed connection between the shaft and the handle. This modular design provides a higher flexibility for the user. In particular, the modular handle is connectable to different shafts with different properties, such as shaft diameter or optical properties, or the same kind of shaft in between individual medical interventions, or during one intervention. Thus, due to the rotatable and connectable interface between the handle and the shaft of a video endoscope, different shafts may be coupled to a single handle, and, alternatively, multiple handles may be connected to the same shaft. Consequently, the shaft is separately cleanable, autoclavable and exchangeable without similar treatment of the handle, whereby the latter is normally not inserted into the cavity of the body and therefore does not require the same cleaning, disinfection and/or sterilization procedures as the shaft.

Given that the electrical and/or mechanical connection of the shaft to the handle is formed inside the handle, and the rotation of the shaft is rotatably supported by the interface portion by means of the at least one bearing, a more generalized and simpler design of the shaft is enabled. Furthermore, as the shaft is detachably connected to the handle, the shaft itself can also be designed to be disposable, while the handle may be reused. This configuration permits the optimization of expense relating to disposable elements by including more costly, but required, elements to be housed in the reusable handle, while the shafts may include only the elements necessary for their function.

Certainly, the invention is not limited to a constant orientation of the handle, also the reverse arrangement is possible where the position of the shaft is hold essentially constant while the handle is rotated. Even the handle and the shaft both can be rotated simultaneously in relation to each other.

Overall, a higher flexibility for the user concerning the exchangeability of the shaft to the modular handle as well as concerning the rotation of the shaft depending on the object field and the preferred hand movement of the user is provided.

One of the primary elements of the invention includes a handle and a video endo scope with a connectable and detachable coupling point between the handle and the shaft of the video endoscope, whereby rotation of the shaft is accomplished independently from the orientation of the handle by supporting the coupling interface portion, to which the shaft is connectable via the second connector element to the first connector element of the interface portion, rotatable via at least one bearing in, at and/or inside the housing of the handle.

As utilized in accordance with the present disclosure, the following terms, unless otherwise indicated, shall be understood to have the following meanings.

In particular, a "video endoscope" (also denominated simply "endoscope") is an endoscope with digital image acquisition and transmission in to the proximal end. The video endoscope comprises a shaft and a handle which are connectable to each other. At least one digital image sensor is located at the distal end of the elongated shaft for image acquisition. A "video endoscope" is any kind of digital endoscope, for example a mediastinoscope, but may also include non-medical scopes used for industrial purposes, often called borescopes.

The "elongated shaft" is in particular a rigid tube, and therefore, the video endoscope may be a rigid endoscope, or, as well, the shaft may be formed by a flexible tube and therefore, a flexible video endoscope is provided. In particular, the shaft is configured for being inserted into a cavity to be viewed endoscopically, for example, to be inserted into a body cavity of a human or animal body or another opening in industrial applications, for example, a pipe. The shaft generally may have an outer diameter in the range of 4 mm to 10 mm. The shaft may comprise one or more channels for irrigation and/or through which working instruments may pass (generally referred to as "working channels") in order to achieve a desired effect in cavity or opening. Preferably, at its distal end, the shaft comprises an electronic image sensor arranged for picking up an image of an object field, whereby the image is generated by an objective lens system. The objective lens system can be arranged at or in a distal end section of the shaft, such that the image is generated on an image sensing surface of the image sensor. The electronic image sensor may be, for example, a charge-coupled device (CCD) or a complementary metal-oxide semiconductor (CMOS). Preferably, the image sensor is configured to convert the captured image into an electrical image signal.

The electronic image sensor, preferably arranged in the distal end section of the shaft, transmits the electrical image signals from the distal end section of the shaft to its proximal end by electrical transmission lines, such as wires, cables and/or a flexible printed circuit board. The transmission is preferably bidirectional, such that electric energy can be supplied and/or control signals transferred to the electronic image sensor. In addition, the generated electrical image signals can be transferred from the electronic image sensor to the proximal end section of the shaft and/or further to the handle and/or an external monitor. Additionally, the bidirectional electrical connection may supply power, in some embodiments, to distally placed illumination means, such as light emitting diodes.

Alternatively, the image sensor may also be positioned in the proximal end section of the shaft and image light collected by the objective lens system may propagate from the distal end section of the shaft to the proximal end section, where the image sensor picks up the image transferred. In this alternative, the shaft comprises a suitable optical image transmission system including, for example, rod lenses for transferring the image light from the distal end section of the shaft to the proximally located image sensor.

Certainly, the video endoscope and/or the shaft may also comprise more than one image sensor being distally or proximally located or even a multiplicity of image sensors, for example three or more image sensors. Multiple image sensors being particularly useful for performing stereo endoscopy, and, in particular, dual image sensors being advantageous for the generation of 3D images.

For the detachable connection to the handle, the shaft comprises at its proximal end section preferably a second connector element. Preferably, the shaft is connected at its proximal end via the second connector element to the first connector element of the interface portion of the handle. In particular, the "first connector element" by the handle and the "second connector element" by the shaft are formed as corresponding counterparts. Especially, the first connector element and the second connector element are each formed in such a manner, that both parts together provide a form-locking connection. For example, the second connector element can be formed as plug and/or male connector and the first connector element can be formed as a female connector and/or a plug socket or vice versa. The first connector element and the second connector element are preferably arranged to be able for a bidirectional transmission.

In particular, the first and second connector elements are configured for transmitting the electric image signal generated by the electronic image sensor to the electric transmission element of the interface portion and for transmitting electric energy and/or control signals from the electric transmission element to the electronic image sensor arranged in the shaft. Consequently, the first and second connector elements are configured for electrically connecting the electric transmission element of the interface portion to the electronic image sensor via a detachable electrical interface.

The coupling point formed by the first connector element and the second connector element preferably enables a non-rotatably connection of the shaft to the interface portion of the handle. Consequently, the shaft is rotatable only in conjunction with the interface portion with respect to the housing and therefore rotatable around the rotational axis of the interface portion relative to the housing. Preferably, the shaft is connectable via the coupling point to the interface portion in such a manner, that a longitudinal axis of the shaft is substantially aligned with the rotational axis of the interface portion, so that the shaft is rotatable around its longitudinal axis together with the interface portion relative to and therefore independent from the orientation of the housing of the handle. Alternatively, the shaft may be configured and the second connector element located such that the longitudinal axis of the shaft forms an angle to the rotational axis of the interface portion.

A "detachable electrical and/or mechanical connection" particularly means that the shaft and the handle can be easily separated and disconnected from each other. In particular, the shaft can be detached from the interface portion and therefore the handle without use of any tool and, more preferably, easily by hand of the user immediately before, during or after an endoscopic intervention or examination.

A "handle" is, in particular, an object that can be moved and/or used by hand, enabling the user to exploit the connected tool and/or instrument for its function. A handle is especially a part of a video endoscope. In particular, the handle comprises a housing and an interface portion which is mounted rotatably via at least one first bearing relative to the housing. Especially, the handle is a modular handle, which can be connected to different kinds of shafts to provide a video endoscope. The handle enables the user to grab, hold and/or operate and manipulate the connectable shaft and therefore the video endo scope. The handle may comprise a grip or grip portion to facilitate holding the handle by the user. Preferably, at its outer surface, for example on the top side or a side face, the handle comprises one or more control elements, such as user buttons or touch keys, for controlling various functions of the endoscope. Preferential, the control elements are arranged and/or located in such a manner on and/or in the surface of the handle that the user can operate the control elements with one or more fingers of the same hand which is holding the handle.

The "interface portion" is a separate part of the handle which is rotatably mounted relative to the housing of the handle. The interface portion has an exterior, which may be an outer surface of a body of the interface portion. In particular, the exterior of the interface portion may be formed by an outer surface of the interface portion in such a way that a proximally rotational symmetry with respect to the rotational axis is given. The exterior may be or comprise a continuous face or may be discontinuous, for example having a grid surface. The interface portion might be formed from solid material. The interface portion may comprise an interior hollow space for including the electric transmission element or other parts. For example, the interface portion can be formed as a hollow cylinder with one face side or both face sides closed. Preferably, at the distal end and/or at and/or inside the distal end section of the interface portion, the first connector element is arranged.

Additionally, at its distal end or end section, the interface portion and/or the housing of the handle may comprise a claw for forming a claw coupling. Preferably, the interface portion is mounted and supported by at least one bearing in the housing. Hereby, the interface portion may be mounted partially or completely inside the housing, for example in an opening or a partially open cavity of the housing. Therefore, the interface portion may be covered by the housing completely besides the distal face side with the attached first connector element. Alternatively, the interface portion could be mounted in such a manner, that at least a section of its exterior forms a part of an exterior of the handle. However, at least a section of the exterior of the interface portion or the majority of the interface portion may be enclosed or encompassed by the housing of the handle.

The "transmission element" is an electric and/or electronic element to which the first connector element is electrically connected. Furthermore, the electric transmission element is particularly connected to the electrical connection assembly arranged at an exterior of the interface portion. Thus, the electric transmission element is an intermediate element for transmission of electric energy and/or signal and/or control data between the first connector element and the electrical connection assembly, whereby, from the electrical connection assembly, the signal data is transferred further to the stationary electric and/or electronic component. Reversely, the electric power and/or control signals are transmitted from the stationary electric and/or electronic component via the electrical connection assembly to the electric transmission element of the interface portion and further via the first connector element and the second connector element towards the shaft. Therewith, the first and second connector elements are cooperating and being connected to form a detachable electric connection between the electric transmission element of the interface portion and the electronic image sensor in the shaft. The electric transmission element of the interface portion may be, for example, one or several cables, a multi-wire cable or a printed circuit board (PCB) having conductor tracks for transmitting electric signals and/or energy. Preferably, the interface portion, apart from the electric transmission element and the electrical connection assembly, comprises no further electric or electronic parts and no control and/or processing element. Alternatively, the electronic transmission element of the interface portion may comprise image pre-processing circuitry or other components.

An "electrical connection assembly" is an electric component for featuring an electric connection between the interface portion and a stationary electric and/or electronic component. The electrical connection assembly comprises at least one electric component or several electric components. The electrical connection assembly is configured for transmission of the electric image signals from the electric transmission element of the interface portion to the stationary electronics of the handle, and/or for transmitting electric energy and/or control signals from the stationary electronics of the handle to the electric transmission element of the interface portion. In particular, the electrical connection assembly is arranged at the exterior of the interface portion and forms an electrical connection in a multiplicity of rotational positions of the interface portion relative to the housing. Hereby, the electrical connection assembly is configured to maintain the electrical connection in various rotational positions of the interface portion to the housing without interruption. In particular, the electrical connection assembly may be configured to provide the electric connection independently from the rotational position or from a corresponding rotation angle of the interface portion, at least in a given range of rotational positions. Consequently, the electrical connection assembly forms an electrical connection between the electric transmission element of the rotatable or rotating interface portion and the stationary, non-rotatable electronics of the handle. Preferably, the electrical connection assembly is configured in such a manner, that it copes with the rotational movement of the interface portion without permitting an influence of the rotation on the electrical connection and, therefore, guaranteeing a high-quality connection. The electrical connection assembly may have a first end or part that its connected to or is configured to contact the exterior, for example connected to or connecting an outer surface, of the interface portion and a second ends or element that is connected to the stationary electronics of the handle, wherein the first and second end are electrically connected or contacted to each other. For example, the electrical connection assembly can be a sliding contact consisting of a brush and a slip ring or may be a flexible conductor element, such as a flexible ribbon cable or a flexible circuit board.

A "bearing" is, in particular, a machine element that constrains relative motion to only the desired motion and reduces the friction between moving and/or stationary parts. The bearing may provide free rotation of the interface portion around its rotational axis and/or the rotational axis of the bearing. In particular, the bearing is a rotary bearing which holds and supports the interface portion at and/or in the housing. The bearing is, for example, a rolling element bearing or a plain bearing. For supporting the interface portion in the housing, it is possible to use only one bearing, e.g. a plain bearing, where the other part of the bearing is formed by the interface portion or the housing.

In a further embodiment, the handle comprises a second bearing for rotatably supporting the interface portion, wherein the first and the second bearings are arranged in a distance to each other in a direction along a rotation axis of the interface portion.

Thus, a load specific, rotatable support of the interface portion in the housing is provided. Hereby, the load by the connectable shaft can be absorbed and distributed by two bearings improving a smooth rotating of the shaft and the electrical and/or mechanical connection between the shaft and the interface portion. Consequently, a rotatable, reliable transmission of supplied energy and signal as well as control data is guaranteed.

The "second bearing" is a bearing as defined above.

A "rotation axis" is, in particular, a straight line around which a body can rotate without changing the view of the body. Preferably, the rotation axis is also an axis of symmetry of the body. The rotation axis of the interface portion can be identical to the rotation axis of the center of the first and/or second bearing. Likewise, the rotation axis of the interface portion can be identical to the longitudinal axis of the interface portion and/or the shaft. Various shaft lengths may used according to the present invention, depending on bearing positions. As an example, in certain implementations, a center-to-center distance between the bearings might be 23.5 mm, and such a configuration might correspond to a complete shaft length (from the end of the bearing to the distal tip of the shaft) of 370 mm and a functional shaft length (from the end of the clasping mechanism to the distal tip of the shaft) of 300 mm, that is, the bearing distance is approximately 5.14% of the complete shaft length and 7.38% of the functional shaft length.

In order to fit the first and/or second bearing tightly between the housing and the interface portion of the handle and/or to specifically surround a cylindric interface portion, the first and/or the second bearing comprises or comprise an outer ring surface and an inner ring surface, wherein the outer ring surface is arranged at an inner surface of the housing and the inner ring surface is arranged at an outer peripheral surface of the interface portion.

Thus, the outer ring surface is stationary attached to the housing, while the inner ring surface rotates, allowing the rotation of the supported interface portion at the inner ring surface and therefore the rotation of the connectable shaft. In case of a cylindric interface portion, preferably the inner ring surface is arranged directly around the outer peripheral surface of the cylindric interface portion for rotating the interface portion and the connectable shaft. Alternatively, the interface portion comprises a drive shaft, which is supported by the bearing or bearings. Certainly, one bearing or the bearings can also be arranged such, that the shaft is fixed in its orientation and the handle is rotatable or that the shaft and the handle can be both rotated simultaneously relative to each other.

In yet another embodiment of the invention, the first and/or second bearing is and/or are rolling-element bearing and/or a plain bearing.

Therefore, the interface portion can be rotatably supported in the housing by a rolling-element bearing alone or a plain bearing alone or by two rolling-element bearings, two plain bearings or a mixed support by one rolling-element bearing and one plain bearing. As a plain bearing mostly takes radial forces, two rolling-element bearings can be more advantageous in case of high loads by the shaft and for reducing friction losses. In particular, the advantages of ball bearings are that this kind of bearings can absorb likewise radial and/or axial forces.

A "rolling-element bearing" is a bearing in which rolling-elements are placed between the turning and the stationary races preventing sliding friction. A rolling-element bearing can be a bearing in which the rolling-elements are spherical balls. Likewise, a rolling-element bearing can be a roller bearing, in which the rolling-elements are cylindrical, tapered and/or spherical rollers.

A "plain bearing" is, in particular, a bearing consisting of a shaft rotation in a hole. In a plain bearing, especially the shaft is sliding over and/or rotating relative to the bearing surface. In case of a plain bearing, either the shaft is connected to the interface portion, for example to the face side of the interface portion at the proximal end, or the interface portion itself constitutes the shaft and slides directly inside the surrounding bearing surface of the plain bearing.

As forces acting on the electrical and/or mechanical connection between the shaft and the interface portion of the handle result mostly from the movement of the shaft in the cavity during use of the video endoscope, the first or the second bearing has a length in the direction along the rotational axis of the interface portion in such a manner or the distance between the first and the second bearings is arranged in such a manner, that the load force from outside the bearing or bearings is absorbable by the bearing or bearings.

Therefore, in case of one plain bearing, the length of the plain bearing in the direction along the rotation axis of the interface portion can be adapted, so that forces from the shaft and especially a lever action are minimized and/or absorbed. Likewise, two bearings can be arranged in an optimal distance to each other for best taking of the acting forces during the use of the video endoscope.

In another embodiment of the invention, the first and the second bearings are mounted in an O-modification, so that a center of force is shifted towards the associated elongate shaft and/or a proximal end of the handle protecting the first connector element, the second connector element and/or the electrical connection assembly of the handle.

Therewith, load specific coupling point bearings are provided which connect the rotatable interface portion and/or shaft with the housing of the handle and simultaneously protecting the electrical and/or mechanical connection between the shaft and the handle as well as the electrical connection assembly of the handle from too high forces.

By bracing the two bearings towards each other, an O-modification is achieved with force flow lines surrounding the first connector element, the second connector element and/or the electrical connection assembly, whereby the center of pressure of the video endoscope is further extended along its shaft. Consequently, the load on the first and second connector element as well as on the electrical connection assembly is decreased and forces from outside the bearing region are optimally absorbed. In case of a video endoscope with a rigid shaft, greatest forces typically act at its distal end. By the O-modification, the load bearing points are moved to the load application points as close as possible. Therefore, the point of load application and the point of load bearing are located outside the bearing regions and preferably close together. The point of load application is located at the shaft of the video endoscope and the point of load bearing is also shifted towards the shaft, notwithstanding that the bearing itself is realized in the handle.

Due to the optimal absorption of the load by the bearings, especially in the O-modification, the attached shaft can be more easily rotated relative to the handle. Thus, the connected shaft can be rotated easily and quickly by the user in the cavity during an intervention and use maintaining an upright, vertical position of the handle.

For an optimal load protection of the electrical connection assembly, the first bearing and the second bearing are located on both sides of the electrical connection assembly arranged at the exterior of the interface portion or the outer periphery surface of the interface portion.

In a further embodiment of the handle, the housing comprises a seal for sealing the interface portion at its distal end in the housing.

Therefore, the seal is provided to seal an opening of the housing, in which the interface portion is rotatably mounted. Preferably, the seal is located adjacent to a bearing, such that the bearings are comprised in a sealed inner space of the housing. Most preferably, the seal is arranged at an outside direction from the first and second bearings, such that the region of the outer peripheral surface and/or the electrical connection assembly is enclosed by the seal. Such a seal can protect the handle, particularly any electric and electronic components and/or connections within the handle and/or the interface portion, such as, in particular, the electrical connection assembly, from body liquid, other liquids and/or sterilization fluids. Therefore, the sealing may improve the durability and operational safety of the handle and the video endoscope.

For an optimal bracing of the bearings and therefore optimal protection by the bearings, the first bearing is located between the seal and the electrical connection assembly and/or the second bearing is located at a proximal end of the interface portion.

In a further embodiment of the handle, the electrical connection assembly comprises at least one flexible conductor element.

By the flexible conductor element, a flexible and therefore moveable connection is provided between the electric transmission element and a stationary electric and/or electronic component of the handle. Further, this electrical connection can be maintained in a multiplicity of rotational positions of the shaft or, in particular, in any orientation of the shaft relative to the housing of the handle.

A "flexible conductor element" is, in particular, a flexible ribbon cable, a flexible elongate circuit board and/or any other flexible electric connection. The flexible conductor element can be twisted around its longitudinal direction and/or can be spooled. A ribbon cable or a flexible circuit board may comprise a multiplicity of electric leads, permitting transmission of a high data volume and/or several signals in parallel, as well as supplying energy to the image sensor in the shaft.

For allowing a simple, reliable and reproduceable electric connection of the handle and therefore reliable and reproduceable operation of the video endoscope, the at least one flexible conductor element is configured to be spooled on and/or unspooled from the exterior or outer peripheral surface of the interface portion by rotating the interface portion relative to the housing.

By this embodiment, the rotatability is electrically realized by the spooling and/or unspooling of the flexible conductor element, such as a flexible circuit board, around and/or from the outside of the interface portion, whereby the flexible conductor element is the intermediate electrical connection element between the first connector element and the electric transmission element on the distal side of the handle and the stationary electric and/or electronic component of the handle. Consequently, the user is free to choose a suitable orientation of the shaft without substantially impeding the electrical connection between the image sensor in the shaft and an image processing unit connected to the stationary electric component arranged in the handle or outside the handle.

In particular, the flexible conductor element is wrapped or wound around the section of the periphery or the outer peripheral surface of the interface portion or a respective frame or spool arranged at the outside of the interface portion, when the interface portion is rotated by handling the shaft in one direction, and wound off when the interface portion is rotated in the opposite direction. Hereby, the interface portion and the flexible conductor element can directly form a spool.

The flexible conductor element may have a first end that is fixed to the outer peripheral surface and electrically connected to the electric transmission element of the interface portion, and a second end that is mounted to the housing and connected to the stationary electric and/or electronic component of the handle. Most preferably, the flexible conductor element is mounted and/or arranged such that a twisting is avoided when it is spooled or unspooled. Consequently, the electric connection can be maintained by the flexible conductor element in an uninterrupted manner during rotation and for any rotational position of the interface portion in a pre-defined range of rotational positions under low friction forces. Preferably, the interface portion or the flexible conductor element are configured such that the flexible conductor element can be wound at least 90°, at least 180°, at least 270° or at least 360° around the outer periphery of the interface portion, at least a rotation is permitted in a corresponding range of rotational positions. Hereby, the flexible conductor element may carry out more than one complete winding when it is wound around the circumference of the interface portion or may form one complete winding or more than one winding. Preferably, in case of several windings, each winding may be wound one on the other, forming a spiral-shaped arrangement. Consequently, a high degree of rotational freedom and a substantially whirl-free operation of the handle and therefore enhanced functionality and durability of the video endoscope is provided.

As the flexible conductor element can be spooled around the outer surface of the interface portion and/or arranged between the space between the two bearings as a reservoir, a space-saving arrangement and therefore a compact and ergonomic design of the handle is achieved. Accordingly, the video endoscope permits easier handling and configuration as well as improved functionality and operational safety.

Preferably, the flexible conductor element is completely contained in the housing of the handle, especially in a provided sufficient space in a reservoir. Furthermore, for avoiding entangling or blocking of the flexible conductor element during spooling and/or unspooling, the flexible conductor element is guided by a guidance mean, such as a roll.

In yet another embodiment, the handle comprises at its distal end a claw coupling for holding a coupling plate, in particular eyepiece cup, of the associated shaft and for securing the connection between the associated shaft and the handle.

In the connected state, the coupling plate and/or the eyepiece cup is pressed by the claw and therewith the complete shaft against the interface portion. By this mechanical claw coupling, an additional mechanical connection with a greater connecting surface than the first and the second connector elements is provided. Consequently, the shaft is additionally secured at the housing and/or interface portion of the handle.

A "claw coupling", also called dock-clutch, is in particular a clutch that couples two components, whereby at least one or both components are rotatable, by interference or clearance fit. Preferably, the claw of the claw coupling is designed such that the coupling plate and/or the eyepiece cup is pushed towards the interface portion, while both the shaft with the coupling plate and/or eyepiece cup and the interface portion are rotating at the same speed without slip.

In an additional aspect of the invention, the problem is solved by a video endoscope, in particular medical or industrial video endoscope, comprising an elongate shaft, wherein the elongate shaft comprises at least one electronic image sensor, a second connector element at a proximal end section of the shaft, which is electrically connected to the at least one electronic image sensor and is detachably connected to a handle, and/or a coupling plate, wherein the handle is a handle as described above, so that the first connector element of the handle and the second connector element of the handle form a detachable electrical and/or mechanical connection and the shaft is rotatable via the rotatably supported interface portion relatively to the housing of the handle.

Therewith, a rotatable and connectable video endoscope is provided with a load specific support of the shaft at and/or in the handle including load specific bearings for the rotatability.

Certainly, the handle is not restricted to a specific kind of video endoscope and can be connected to any kind of shaft for forming the video endoscope or a conventional endoscope. Besides that, the handle can be used to form any kind also of conventional endoscopes, the handle is specifically designed for forming a video endoscope with each connected shaft.

Therefore, a video endoscope is provided which can be used and operated by the handle in an easy and efficient way by the user.

In a further embodiment of the video endoscope, the first connector element of the interface portion of the handle and the second connector element of the shaft form a bidirectional electric connection.

Thus, control signals and energy can be transmitted from the handle of the video endoscope to the shaft and the image sensor located in the shaft and reversely image signals and data can be transferred from the shaft to the handle and further to the outside of the video endoscope.

Therefore, electronic image data can be transferred bidirectionally via the rotatable, electric connection between the handle and the shaft.

In a further aspect of the invention, the problem is solved by a connectable and detachable shaft as described above to the handle.

As the bearing concept of the invention is realized in the handle of the couplable endoscope, the shaft can be realized more generalized and/or permits a simpler, disposable design. Furthermore, the shaft can be disconnected and reused and can undergo a special disinfection and/or sterilization treatment independent from the handle. For this, especially the proximal end of the shaft is hermetically sealed and therefore in particular autoclavable allowing multiple use of the shaft.

Alternatively, the shaft may be configured disposable and therefore for single use. In particular, the shaft may comprise only a small number of costly optical and electronic elements and thus may be designed to be manufactured at comparatively low costs.

In contrast, the handle is configured normally for multiple use, as the handle is not introduced into the cavity of a body during the endoscopic intervention, the handle does not necessarily have to be autoclavable.

In a further aspect of the invention, the problem is solved by a method for configuring a video endoscope, including the steps of providing a handle and a shaft being configured as described above, wherein the shaft is connected to the handle electrically and mechanically, as described above, to form the video endoscope to be operatable.

In a subsequent method step to be performed after the use of the video endoscope, the shaft may be detached from the handle as described above. In a further step, another shaft may be connected to the handle or the shaft and the handle may be subject to cleaning and/or sterilization. Both the shaft and the handle may be reusable, the shaft preferably autoclavable.

BRIEF DESCRIPTION OF THE DRAWINGS

The invention is further explained by the following exemplary description of particular embodiments.

DETAILED DESCRIPTION OF THE INVENTION

Figure 1:
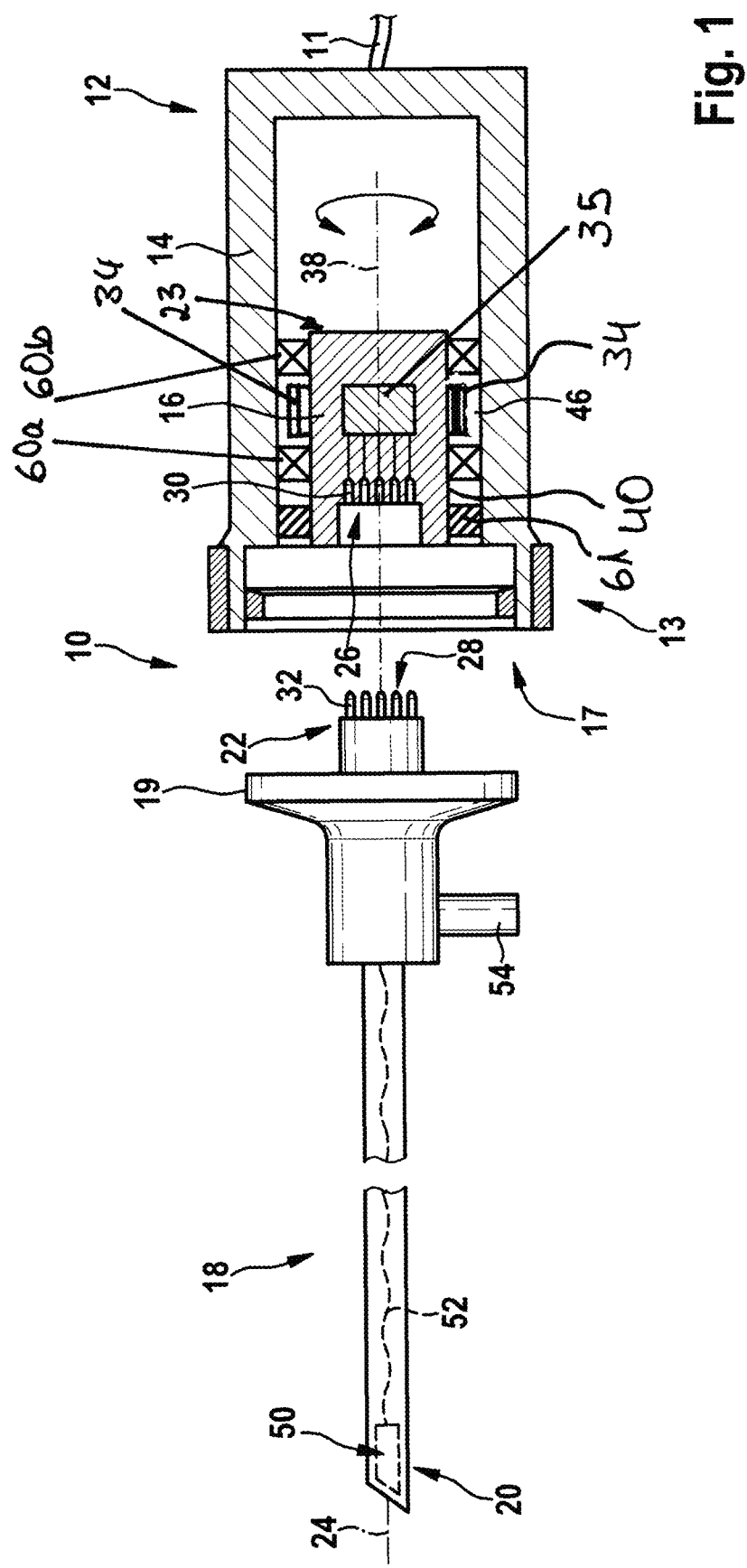
FIG. 1 is a schematic, partially sectional view of a shaft and a handle of a video endoscope in a detached state.

A video endoscope 10 comprises a handle 12 and a shaft 18 connectable to each other. The handle 12 and the shaft 18 are shown in FIG. 1 in a detached state and in FIGS. 2 to 4 in a connected state. The video endoscope 10 is designed to provide video and image data from an object field within a cavity of a non-shown body. The handle 12 of the video endoscope 10 is connected via a cable 11 at its proximal end to an external control and supply system providing electric power and comprising image processing and displaying means via a computer and a monitor.

Figure 2:
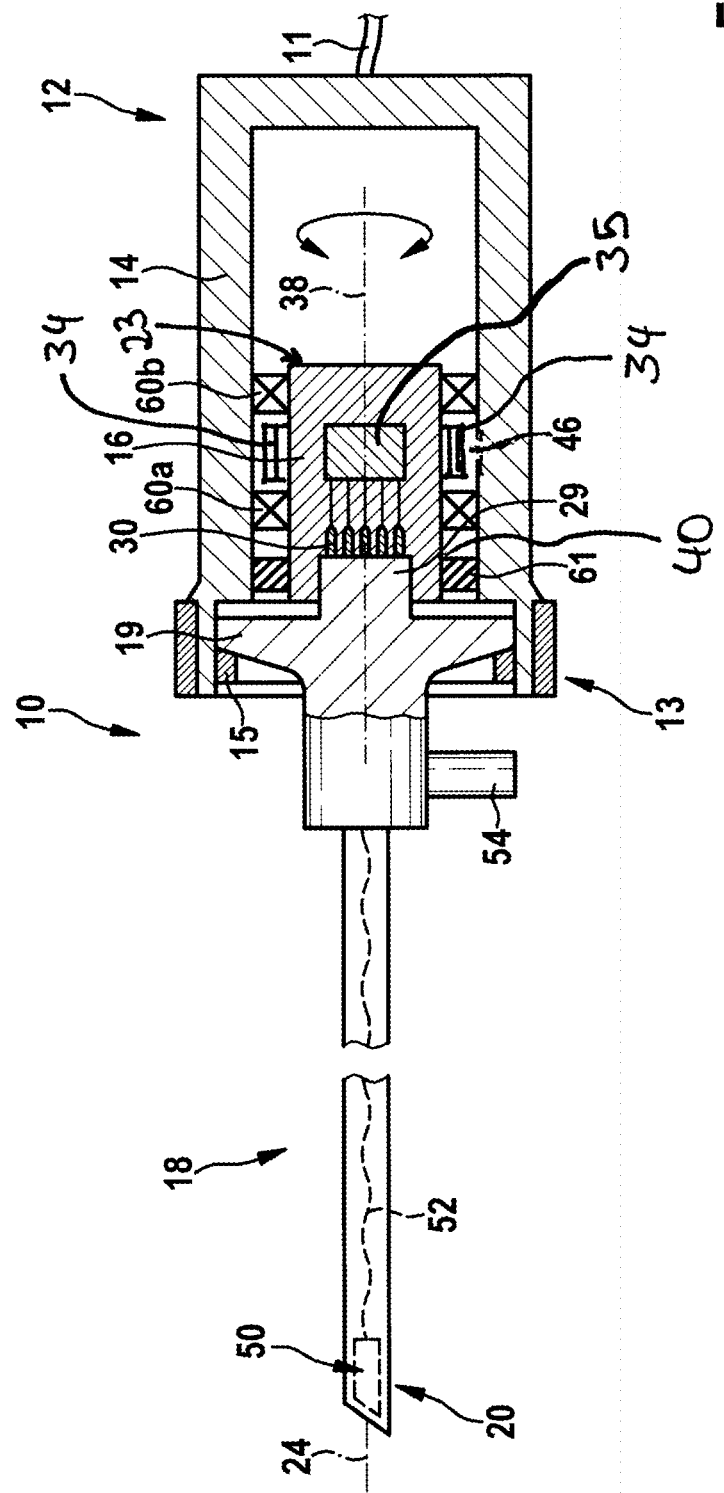
FIG. 2 is a schematic, sectional view of the video endoscope of FIG. 1 in a connected state.
Figure 3:
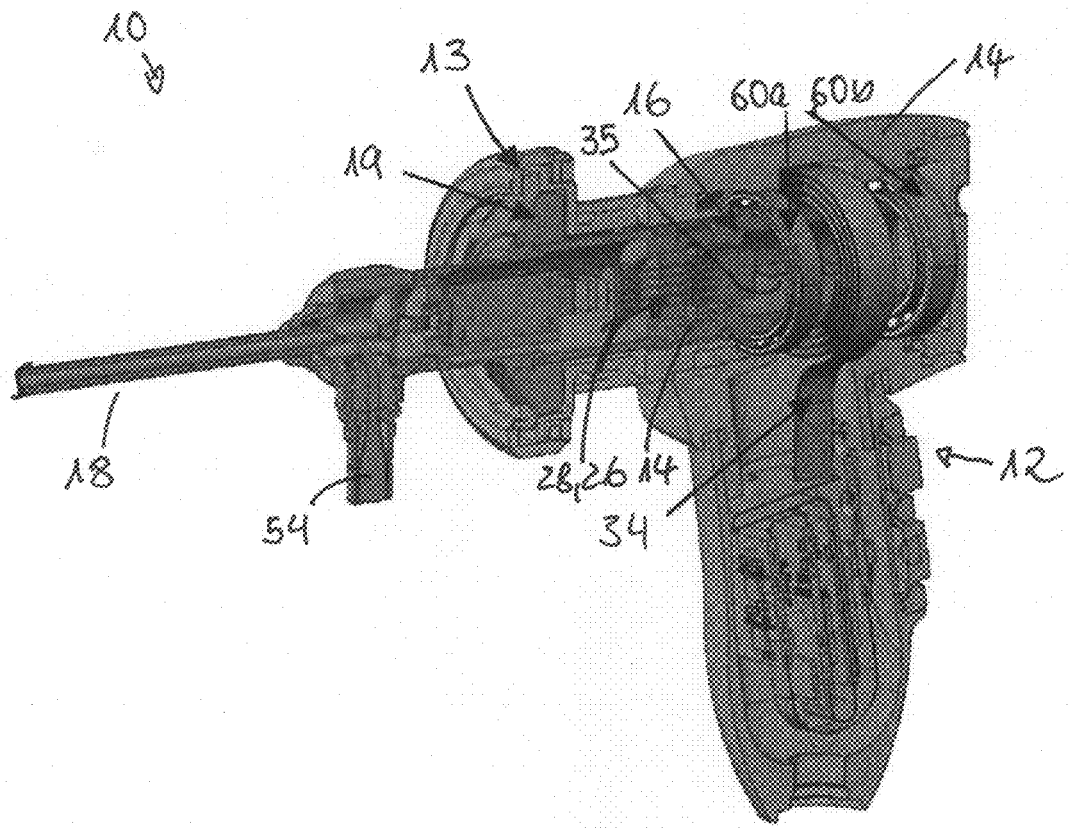
FIG. 3 shows a three-dimensional view of a cross-section of the shaft and the handle of the video endoscope in a connected state.
Figure 4:
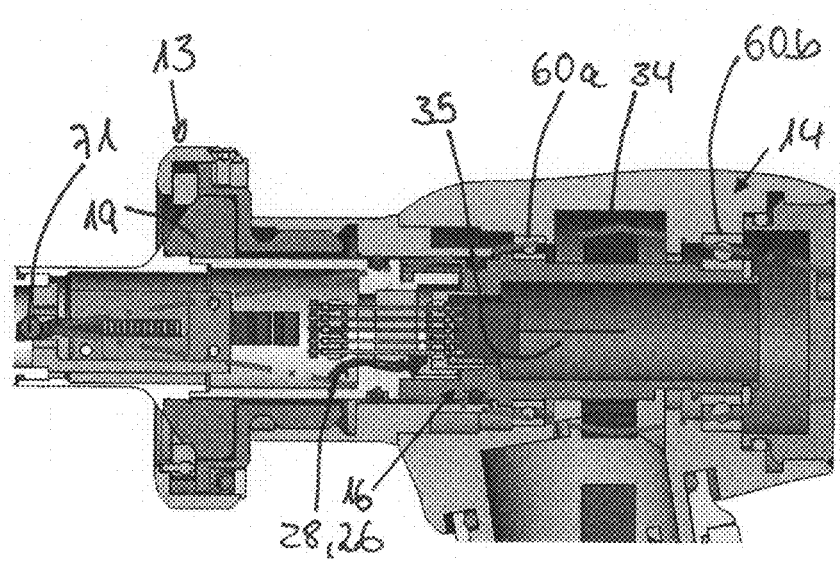
FIG. 4 is a detail of the cross-section of the shaft connected to the handle with two ball bearings in O-modification.

In FIGS. 1 and 2, the handle 12 is only shown in a schematic longitudinal section view without any specific shape to be held by a user of the video endoscope 10, as shown in FIGS. 3 and 4. The handle 12 of the video endoscope 10 comprises a housing 14 and an interface portion 16. At a distal end 17 of the handle 12, the housing 14 has an opening in which the interface portion 16 is mounted. Hereby, the interface portion 16 is sealed by an O-ring seal 61 in the housing 14.

The interface portion 16 is rotatably supported by a first ball bearing 60a and a second ball bearing 60b, which are arranged between an inner surface of the housing 14 and a peripheral surface 40 of the interface portion 16 in a radial direction. In a direction of the rotation axis 38 the first ball bearing 60a is arranged between the seal 61 and a flexible circuit board 34, while the second ball bearing 60b is arranged on an opposite side of the flexible circuit board 34 at a proximal end 23 of the interface portion 16. The interface portion 16 respectively has a cylindric shape. By the two ball bearings 60a and 60b, the interface portion 16 is rotatably supported relative to the housing 14. By the cylindric shape of the interface portion 16, the axis of its cylinder approximately coincides with the rotation axis 38 of the interface portion 16 and likewise with a longitudinal axis 24 of the shaft 18.

Between both ball bearings 60a and 60b, the housing 14 comprises a reservoir 46 for receiving and storing a portion of a flexible circuit board 34.

At its distal end, the interface portion 16 comprises a first connector element 26 with a plurality of sockets 30. The sockets 30 of the first connector element 26 are electrically connected to a PCB (printed circuit board) 35 by a multiplicity of leads (shown in FIGS. 1 and 2 without reference numerals). Further, for the electric connection, the flexible circuit board 34 is arranged on the outer peripheral surface 40 of the interface portion 16, whereby a first end of the flexible board 34 is fixed to a section of the peripheral surface 40 and, at a second end, non-shown conductor tracks of the flexible board 34 are connected to the PCB 35 by non-shown leads in FIGS. 1 and 2. Therefore, the PCB 35 serves as an electric transmission element between the first connector element 26 and the flexible circuit board 34.

Furthermore, the handle 12 comprises at its distal end a claw coupling 13 with a claw 15 for engaging with an eyepiece cup 19 of the shaft 18.

The elongate shaft 18 comprises a distal end 20 and a proximal end 22, whereby the longitudinal axis 24 extends between the distal end 20 and the proximal end 22 and the proximal end 22 is hermetically sealed. At its distal end 20, the shaft 18 comprises an imaging unit 50 including an objective lens system and an electronic image sensor. The imaging unit 50 is connected via a multi-wire cable 52 through the shaft to a second connector element 28 that is arranged at the proximal end 22 of the shaft 18. A second connector element 28 comprises a plurality of conductor pins 32, whereby only five pins 32 are shown symbolically in FIGS. 1 and 2. The pins 32 of the second connector element 28 of the shaft 18 and the sockets 30 of the first connector element 26 are designed contrarily, whereby the pins 32 and the sockets 30 extend parallel through the rotation axis 38 of the interface portion 16 and the pins 32 can be inserted in the direction towards a proximal end 22 of the interface portion 16 into the respective sockets 30.

Furthermore, the shaft 18 has an eyepiece cup 19 at its proximal end 22 and a section with a light post 54 forming a port for connecting a light cable of an external light source and a light guide (not shown) extending in the shaft 18 until the distal end 20 of the shaft 18 to transmit illumination radiation provided by the external light source towards an object field to be observed. This section with the light post 54 of the shaft 18 can be handled by the user of the video endoscope 10 by hand for rotation of the shaft 18.

For connecting the shaft 18 to the handle 12, the following steps are carried out:

The shaft 18 is held by one hand and the handle 12 by the other hand by the user aligning the longitudinal axis 24 of the shaft 18 with the rotational axis 38 of the interface portion 16 of the handle 12. The proximal end 22 of the shaft is moved towards the distal end 17 of the handle 12. Guided by the claw coupling 13 with the claw 15, the pins 32 of the second connector element 28 are inserted into the respective sockets 30 of the first connector element 26 giving a mechanical and electrical connection of the shaft 18 to the handle 12. Hereby, the first and the second connector element 26, 28 are held to each other by friction fit of the pins 32 in the sockets 30. Furthermore, the mechanical connection is secured by the claw 15 pressing the eyepiece cup 19 of the shaft 18 firmly but rotatably and releasably to the housing 14 by featuring the claw coupling 13. Due to the form-fitted connection of the first and second connector element 26, 28 by the pins 32 and sockets 30, the shaft 18 itself is not rotatably connected to the interface portion and, therefore, the shaft 18 can only rotate together with the interface portion 16. Consequently, a rotatable and couplable video endoscope 10 is formed by the connection of the shaft 18 to the handle 12.

The two ball bearing 60a and 60b are arranged on both sides of the flexible circuit board 34, which is spooled around the peripheral surface 40 of the handle 12 (see FIG. 3). The first ball bearing 60a and the second ball bearing 60b are braced to each other in an O-modification giving two respective lines of flux 69 with two centers of pressure 51 arranged on both sides along the rotational axis 38 of the interface portion 16 and therewith outside of the connection and bearing region.

The shaft 18 is inserted by the user of the video endoscope 10 into the cavity of the body. Hereby, the shaft 18 is rotated by hand at the section of the light post 54 of the shaft 18 effecting a rotation of the shaft 18 together with the interface portion 16 due to the rotatable support by the two ball bearings 60a and 60b of the interface portion 16 in the housing 14 in order to achieve the desired object fields. The respective images captured by the electronic image sensor of the imaging unit 50 are transferred as image data via the multi-wire cable 52 through the shaft 18 to the connected second connector element 28 and further transmitted via the pins 32 and the sockets 30 of the first connector element 26 to the PCB 35, from the PCB 35 to the flexible circuit board 34 spooled around the peripheral surface 40 of the interface portion 16 and further by the cable 11 of the handle 12 to the external control and supply system to be viewed on the monitor. By the respective clockwise rotation of the shaft 18 and the interface portion 16, a section of the flexible circuit board 34 is unspooled into the reservoir 46.

Due to the arrangement and bracing of the first ball bearing 60a and the second ball bearing 60b in an O-modification with the respective lines of flux 66, the first and second ball bearing 60a, 60b on both sides of the flexible circuit board 34 arranged between the housing 14 of the handle 12 and the interface portion 16 optimally absorb the forces from using the shaft 18 with centers of pressure 71 shifted to the distal end 17 of the handle and further towards the shaft 18 on one side and towards the proximal end of the handle 12 on the other side.

Therefore, a video endoscope 10 is provided with a rotatable and detachable shaft 18 and a load specific coupling due to the ball bearings 60a, 60b protecting the mechanical and electrical connection between the shaft 18 and the interface portion 16 of the handle 12 and therewith the first connector element 26, the second connector element 28 and the flexible circuit board 34 from load impact and damages.

REFERENCE NUMERALS

10 Video endo scope
11 Cable
12 Handle
13 Claw coupling
14 Housing
15 Claw
16 Interface portion
17 Distal end of handle
18 Shaft
19 Eyepiece cup
20 Distal end of shaft
22 Proximal end of shaft
23 Proximal end of interface portion
24 Longitudinal axis
26 First connector element
28 Second connector element
30 Socket
32 Pin
34 Flexible circuit board
35 PCB
38 Rotation axis
40 Peripheral surface
46 Reservoir
50 Imaging unit
52 Cable
53 Leads
54 Light post
60a First ball bearing
60b Second ball bearing
61 Seal
67 Distance
69 Line of flux (O-modification)
71 Center of pressure

The invention claimed is:

1. A handle for a video endoscope comprising a housing and an interface portion, wherein the interface portion comprises a first connector element at its distal end, the first connector element is connected to an electric transmission element of the interface portion and is connectable to a second connector element of an associated elongate shaft of the video endoscope to form a detachable electrical and/or mechanical connection between the handle and the associated shaft, and wherein the handle comprises an electrical connection assembly arranged at an exterior of the interface portion forming an electrical connection between the electric transmission element and a stationary electric and/or electronic component of the handle, wherein the handle comprises at least a first bearing for rotatably supporting the interface portion in and/or at the housing, so that in case of a connection between the associated shaft and the handle, the associated shaft is rotatable via the rotatably supported interface portion relatively to the housing of the handle.

2. The handle of claim 1 wherein the handle comprises a second bearing for rotatably supporting the interface portion, wherein the first and the second bearings are arranged in a distance to each other in a direction along a rotation axis of the interface portion.

3. The handle of claim 2 wherein the first and/or the second bearing comprises or comprise an outer ring surface and an inner ring surface, wherein the outer ring surface is arranged at an inner surface of the housing and the inner ring surface is arranged at an outer peripheral surface of the interface portion.

4. The handle of claim 3 wherein the first and/or the second bearing is or are a rolling-element bearing and/or a plain bearing.

5. The handle of claim 4 wherein the first or the second bearing has a length in the direction along the rotation axis of the interface portion in such a manner or the distance between the first and the second bearings is arranged in such a manner, that a load force from outside the bearing or bearings is absorbable by the bearing or bearings.

6. The handle of claim 5 wherein the first and the second bearings are mounted in an O-modification, so that a center of force is shifted towards the associated elongate shaft and/or a proximal end of the handle protecting the first connector element, the second connector element and/or the electrical connection assembly of the handle.

7. The handle of claim 6 wherein the first bearing and the second bearing are located on both sides of the electrical connection assembly arranged at the exterior of the interface portion or the outer peripheral surface of the interface portion.

8. The handle of claim 7 wherein the housing comprises a seal for sealing the interface portion at its distal end in the housing.

9. The handle of claim 8 wherein the first bearing is located between the seal and the electrical connection assembly and/or the second bearing is located at a proximal end of the interface portion.

10. The handle of claim 9 wherein the electrical connection assembly comprises at least one flexible conductor element.

11. The handle of claim 10 wherein the at least one flexible conductor element is configured to be spooled on and/or unspooled from the exterior or outer peripheral surface of the interface portion by rotating the interface portion relative to the housing.

12. The handle of claim 11 wherein the handle comprises at its distal end a claw coupling for holding a coupling plate, in particular eyepiece cup, of the associated shaft and for securing the connection between the associated shaft and the handle.

13. The handle of claim 2 wherein the first and/or the second bearing is or are a rolling-element bearing and/or a plain bearing.

14. The handle of claim 13 wherein the first or the second bearing has a length in the direction along the rotation axis of the interface portion in such a manner or the distance between the first and the second bearings is arranged in such a manner, that a load force from outside the bearing or bearings is absorbable by the bearing or bearings.

15. A video endoscope comprising an elongate shaft and a handle,
wherein, the elongate shaft comprises one or more electronic image sensors, a second connector element at a proximal end section of the elongate shaft that is electrically connected to the one or more electronic image sensors, and is detachably connected to the handle;
wherein the handle comprises a housing and an interface portion, wherein the interface portion comprises a first connector element at its distal end, the first connector element is connected to an electric transmission element of the interface portion and is connectable to the second connector element of the elongate shaft, and wherein the handle comprises an electrical connection assembly arranged at an exterior of the interface portion forming an electrical connection between the electric transmission element and a stationary electric and/or electronic component of the handle, wherein the handle further comprises at least a first bearing for rotatably supporting the interface portion in and/or at the housing, so that in case of a connection between the associated shaft and the handle, the associated shaft is rotatable via the rotatably supported interface portion relatively to the housing of the handle; and
wherein the first connector element of the handle and the second connector elements of the shaft form a detachable electrical and/or mechanical connection and the shaft is rotatable via the rotatably supported interface portion relative to the housing of the handle.

16. The video endoscope of claim 15 wherein the first connector element of the interface portion of the handle and the second connector elements of the shaft form a bidirectional electrical connection.

17. The video endoscope of claim 16 wherein the handle comprises a second bearing for rotatably supporting the interface portion, wherein the first and the second bearings are arranged in a distance to each other in a direction along a rotation axis of the interface portion.

18. The video endoscope of claim 17 wherein the first and/or the second bearing comprises or comprise an outer ring surface and an inner ring surface, wherein the outer ring surface is arranged at an inner surface of the housing and the inner ring surface is arranged at an outer peripheral surface of the interface portion.

19. The video endoscope of claim 18 wherein the first or the second bearing has a length in the direction along the rotation axis of the interface portion in such a manner or the distance between the first and the second bearings is arranged in such a manner, that a load force from outside the bearing or bearings is absorbable by the bearing or bearings.

20. The video endoscope of claim 17 wherein the first or the second bearing has a length in the direction along the rotation axis of the interface portion in such a manner or the distance between the first and the second bearings is arranged in such a manner, that a load force from outside the bearing or bearings is absorbable by the bearing or bearings.

* * * * *